US009663931B2

(12) United States Patent
Withrington

(10) Patent No.: US 9,663,931 B2
(45) Date of Patent: May 30, 2017

(54) MARINE SANITISING AND DEODORISING DEVICE

(76) Inventor: Derek Withrington, Christchurch (GB)

( * ) Notice: Subject to any disclaimer, the term of this patent is extended or adjusted under 35 U.S.C. 154(b) by 585 days.

(21) Appl. No.: 13/820,797

(22) PCT Filed: Sep. 6, 2011

(86) PCT No.: PCT/GB2011/051661
§ 371 (c)(1),
(2), (4) Date: Mar. 5, 2013

(87) PCT Pub. No.: WO2012/032339
PCT Pub. Date: Mar. 15, 2012

(65) Prior Publication Data
US 2014/0157504 A1    Jun. 12, 2014

(30) Foreign Application Priority Data

Sep. 9, 2010 (GB) .................................. 1014999.5

(51) Int. Cl.
| | | |
|---|---|---|
| E03D 9/02 | (2006.01) |
| E03D 11/00 | (2006.01) |
| E03D 9/00 | (2006.01) |
| A61L 2/18 | (2006.01) |
| B63B 29/14 | (2006.01) |
| E03D 9/03 | (2006.01) |
| G01F 11/00 | (2006.01) |
| G01F 13/00 | (2006.01) |

(52) U.S. Cl.
CPC ............... *E03D 9/005* (2013.01); *A61L 2/18* (2013.01); *B63B 29/14* (2013.01); *E03D 9/031* (2013.01); *G01F 11/00* (2013.01); *G01F 13/006* (2013.01); *A61L 2202/15* (2013.01); *E03D 2009/028* (2013.01)

(58) Field of Classification Search
CPC ........................... B63B 2705/00; E03D 9/031
USPC ........... 4/433, 223, 224, 225.1, 226.1, 227.1
See application file for complete search history.

(56) References Cited

U.S. PATENT DOCUMENTS

| | | |
|---|---|---|
| 5,142,707 A | 9/1992 | Prue |
| 6,000,067 A | 12/1999 | Cascia |
| 6,317,898 B1 | 11/2001 | Mehta |
| 2006/0144800 A1* | 7/2006 | Barreras et al. ............... 210/744 |

(Continued)

FOREIGN PATENT DOCUMENTS

| | | |
|---|---|---|
| AU | 8169594 | 12/1994 |
| DE | 960890 | 3/1957 |
| DE | 202005017056 | 3/2007 |

(Continued)

OTHER PUBLICATIONS

JP 09-105653 A English abstract.*
JP 09-105653 A English machine translation.*
International Search Report PCT/GB2011/051661—Marko Isailovski.

*Primary Examiner* — Christine Skubinna
(74) *Attorney, Agent, or Firm* — Nyemaster Goode, P.C.

(57) ABSTRACT

A marine sanitizing and deodorizing device comprises a reservoir for containing sanitizing fluid, a dose controllable pump for discharging a predetermined dose of sanitizing fluid from the reservoir into a water inlet conduit of a marine toilet system, a flow detector for detecting the flow of water within the water inlet conduit, and a controller for controlling the dose controllable pump upon flow detection by the in use flow detector.

12 Claims, 2 Drawing Sheets

(56) References Cited

U.S. PATENT DOCUMENTS

2009/0204263 A1* 8/2009 Love .................. G05D 23/19
700/282
2010/0205732 A1 8/2010 Muhlhausen

FOREIGN PATENT DOCUMENTS

| | | |
|---|---|---|
| DE | 102007040325 | 2/2009 |
| EP | 0579581 | 1/1994 |
| EP | 1780343 | 3/2007 |
| GB | 021166 | 0/1913 |
| JP | 158315 | 6/1989 |
| JP | 9105653 | 4/1997 |
| WO | 2007009400 | 1/2007 |
| WO | 2009027117 | 3/2009 |

* cited by examiner

MARINE SANITISING AND DEODORISING DEVICE

BACKGROUND

This invention relates to a device for sanitising and deodorising marine toilet systems and their associated pipework, in leisure craft and small commercial craft. More specifically it overcomes the malodorous and foul smelling problems associated with such toilets by controlled injection of biodegradable disinfectant throughout the toilet system, using intelligent control.

In addition, the invention overcomes the ecologically and environmentally unfriendly habit of boat owners pouring large quantities of disinfectant into their marine toilets, in their attempts to control the malodorous and foul smells. These disinfectants are often not easily biodegradable.

Marine toilets typically use seawater, river water or lake water to flush their toilets. This water is drawn from a hull's fitting below the waterline of the boat by means of a manual or electric pump and used to flush the toilet(s). A second manual or electric pump discharges the contents of the toilet bowl into a holding tank or back into the sea, depending upon the proximity of the craft to the shore. Typically, these manual pumping systems are combined into one unit.

These toilet systems are notoriously malodorous and are the bane of many boat owners, particularly when the boat has not been used for a while as they can fill the craft with foul odours.

There are two main reasons for this.
1) The sea or river water drawn into the system contains living organisms which rapidly die and decompose due to lack of oxygen and lack of light in the pipework (or sanitation hose). Anaerobic bacteria take over and create foul smelling sulphurous gases and other compounds, which are then drawn into the toilet bowl during the flushing process and thereby released into the atmosphere inside the craft.
2) The flexible pipework (or sanitation hose) used to plumb marine heads is typically of an expanded flexible PVC material. Bacteria from both the seawater and the urine and faecal matter deposited in the toilet can, over time, penetrate and live inside the structure of the PVC. The outside of the sanitation hose running through the bilges of the craft can therefore also become continuously malodorous.

Although it is possible to partially improve the problem by putting disinfectant into the toilet bowl, this is immediately flushed away with the next flush of the toilet and the bacteria can take over again. More importantly, it is not possible to disinfect the flushing water being drawn into the toilet bowl from the sea or river, by putting disinfectant down the toilet. This is the area where some of the worst problems arise.

Some owners incur great expense by having all of the sanitation hoses on their toilets and holding tanks replaced but within a short period of time the bacteria are back, along with the odour.

Attempts have been made in the past to resolve the problem. U.S. Pat. No. 4,873,727 (17 Oct. 1989); U.S. Pat. No. 5,142,707 (1 Sep. 1992) and U.S. Pat. No. 6,295,657 (2 Oct. 2001) all try to sanitize the incumbent water, by inserting a device into the incoming sanitation hose. This device contains a block of disinfectant/detergent which gradually dissolves and disinfects the water. None of these devices appear to have proved commercially successful for the following reasons.

1) In order to have any effect, the device must be installed close to the inlet seacock and therefore under the waterline of the craft. This involves cutting or drilling holes in the sanitation hose underneath the waterline. Most sensible boat owners would be very wary of doing this as any faulty installation or failure of the device or its fittings could result in the craft sinking.
2) Replacement of the disinfectant block is extremely difficult due to its location in the boat's bilges and potentially dangerous for the reasons stated above. It therefore doesn't get replaced. U.S. Pat. No. 6,295,657 attempts to address this problem but does so by moving the device away from the seacock and thereby leaving long lengths of sanitation hose untreated.
3) If the block is replaced, the seacock has to be closed off and the device opened, thereby allowing the (by now) foul water in the sanitation hose to run out into the bilges of the craft. If the seacock is not properly closed, there is a danger of flooding the boat.
4) The rate of dissolution of the block is not controllable and leads to very concentrated disinfectant being dispensed when the toilet is little used and insufficient, when the toilet is in frequent use. This is also ecologically unfriendly.

SUMMARY

According to a first aspect of the invention there is provided a marine sanitising and deodorising device comprising a sanitising fluid reservoir for containing sanitising fluid, a sanitising fluid dose variable and controllable pump for discharging a predetermined dose of sanitising fluid from the reservoir into a water inlet conduit of a marine toilet system, a flow detector for detecting the flow of water within the water inlet conduit, and a controller for controlling the dose variable and controllable pump upon flow detection by the in use flow detector.

Preferably, the dose variable and controllable pump may be a micro-dosing pump.

Additionally or alternatively, the controller may include a microprocessor for varying the dosage of the micro-dosing pump.

Furthermore, the flow detector may be arranged to be at least partially disposed within the water inlet conduit. In this case, the flow detector may preferably include a moveable gate and a reed switch. Additionally, the moveable gate may optionally include a hinge, said in use moveable gate pivoting about said hinge when liquid flows through the water inlet conduit. Finally, it may be preferable that the moveable gate has a magnet at a free end for activating a magnetic portion of the reed switch.

Preferably, the controller may include a status device for detecting and indicating an amount of sanitising fluid within the reservoir. In this case, the status device may be adapted to emit an alert when the reservoir is or is substantially empty.

Advantageously, the dose variable and controllable pump may include a microbore conduit locatable in the said water inlet conduit and for delivering sanitising fluid to the water inlet conduit.

According to a second aspect of the invention there is provided a marine sanitising and deodorising toilet system comprising a toilet bowl, at least one pump for controlling the flow of water into and/or out of the toilet bowl, a water inlet conduit for delivering water to the toilet bowl, a waste outlet conduit for moving waste from the toilet bowl, and a marine sanitising and deodorising device, the sanitising fluid dose variable and controllable pump being in fluid communication with the water inlet conduit for discharging the sanitising fluid therein when activated by the controller upon flow detection.

Preferably, a microbore conduit of the dose variable and controllable pump extends into the water inlet conduit. In this case, the microbore conduit may extend a long at least a major portion of the longitudinal extent of the water inlet conduit.

Optionally, an outlet of the microbore conduit may be at or proximate an inlet of the water inlet conduit.

The marine sanitising and deodorising toilet system may further comprise a ventable holding tank which is in liquid communication with the water inlet conduit for transport of the water thereto.

There is provided a marine craft having a hull and a marine sanitising and deodorising toilet system as in accordance with the second aspect of the invention an outlet of the waste outlet conduit being provided in the hull and below a waterline of the hull.

Beneficially, the marine craft may further comprise an electrical power system, the marine sanitising and deodorising device of the toilet system being energisable by the power system. Optionally, the controller may monitor the power system and indicates a power level.

There may also be provided a method of sanitising and deodorising a marine toilet system using a marine sanitising and deodorising device, the method comprising the steps of: monitoring flow within a water inlet conduit of a marine toilet system; dispensing a predetermined volume of sanitising fluid into the water inlet conduit; providing the water and sanitising fluid to a toilet bowl; and discharging waste from the toilet bowl into a waste outlet conduit.

Preferably, the method may further comprise the step of monitoring a frequency of usage of the marine toilet system over a period of time. Beneficially, the method may include, upon detection of a pre-determined low frequency of usage, automatically periodically dispensing a predetermined volume of sanitising fluid into the water inlet conduit at or adjacent to an inlet thereof.

Additionally or alternatively, the method may include, upon detection of a pre-determined high frequency of usage, automatically dispensing a reduced volume of sanitising fluid into the water inlet conduit at or adjacent to an inlet thereof. In this case, the method may preferably include the automatic dispensing takes place during use of the marine toilet system.

The present invention uses modern technology to ensure that precise and accurate doses of disinfectant are injected into the inlet flushing water of the marine toilet, so that all of the sanitation hose is disinfected.

For toilets flushed with sea or river or lake or canal water, the disinfectant is injected close to the start of the inlet pipe of the flushing water, by the seacock. This is achieved without any cutting or drilling of the hose or any connections below the waterline.

For marine toilets flushed with fresh (drinking) water from the craft's water tanks, the disinfectant is injected just before the marine toilet.

The device is easily refillable and uses microprocessor technology to adapt the disinfectant quantities dispensed to the usage of the toilet in an ecologically and environmentally friendly way.

The device includes a small housing installed next to the toilet, containing a container of disinfectant, a disinfectant pump, a microprocessor logic board and a battery, or alternatively a connection to the boat's power supply. The housing is preferably plastic. The device is connected via a fine conduit to a combined flow detection device and manifold, mounted on the toilet, just before the flush pump.

The disinfectant pump injects disinfectant through a microbore tube which passes through the conduit, through the manifold and thereby into the toilet's inlet flushing sanitation hose.

When the toilet is flushed the flow detection device sends a signal to the microprocessor that the flush cycle has commenced. The microprocessor then progresses through a series of algorithms; typically a delay of some seconds, then initiating the disinfectant pump to run for a number of seconds, then a lockout period during which further actuations of the flow switch will not have any effect.

In this way, a measured dose of ecologically friendly, biodegradable disinfectant is injected throughout the sanitation hose during the flush and is carried by the flush water through to the flush pump, the toilet, the discharge pump and all of the rest of the system every time it is flushed.

The microprocessor has other important features. If the craft is left unused for a period of time, it would be possible for the disinfectant in the inlet sanitation hose to slowly dilute, via the open seacock.

The microprocessor therefore has a "maintenance cycle" whereby, should the toilet remain unflushed for a period of time, it runs the disinfectant pump for a fixed number of seconds to inject more disinfectant into the inlet sanitation hose, thereby keeping the water sanitized and odour free. The disinfectant disperses and dissolves throughout the inlet sanitation hose.

This mode does not apply to embodiments of the invention supplied for craft which flush their toilets with water from the craft's on board water tanks.

On certain occasions the craft may be subject to long continuous usage, such as a long voyage with a full crew on board. On these occasions the toilet(s) could be subject to heavy usage of 50 or more flushes per day, which would exhaust the disinfectant container quite quickly.

In these circumstances less disinfection to the system is required so the microprocessor registers the high usage and reduces the amount of disinfectant dispensed each flush by reducing the operation of the disinfectant pump. This ecologically friendly feature reduces disinfectant usage and allows the disinfectant to last an acceptable period of time before refilling, during heavy usage.

BRIEF DESCRIPTION OF THE DRAWINGS

The invention will now be more particularly described, by way of example only, with reference to the accompanying drawings, in which.

DETAILED DESCRIPTION

Figure 1:
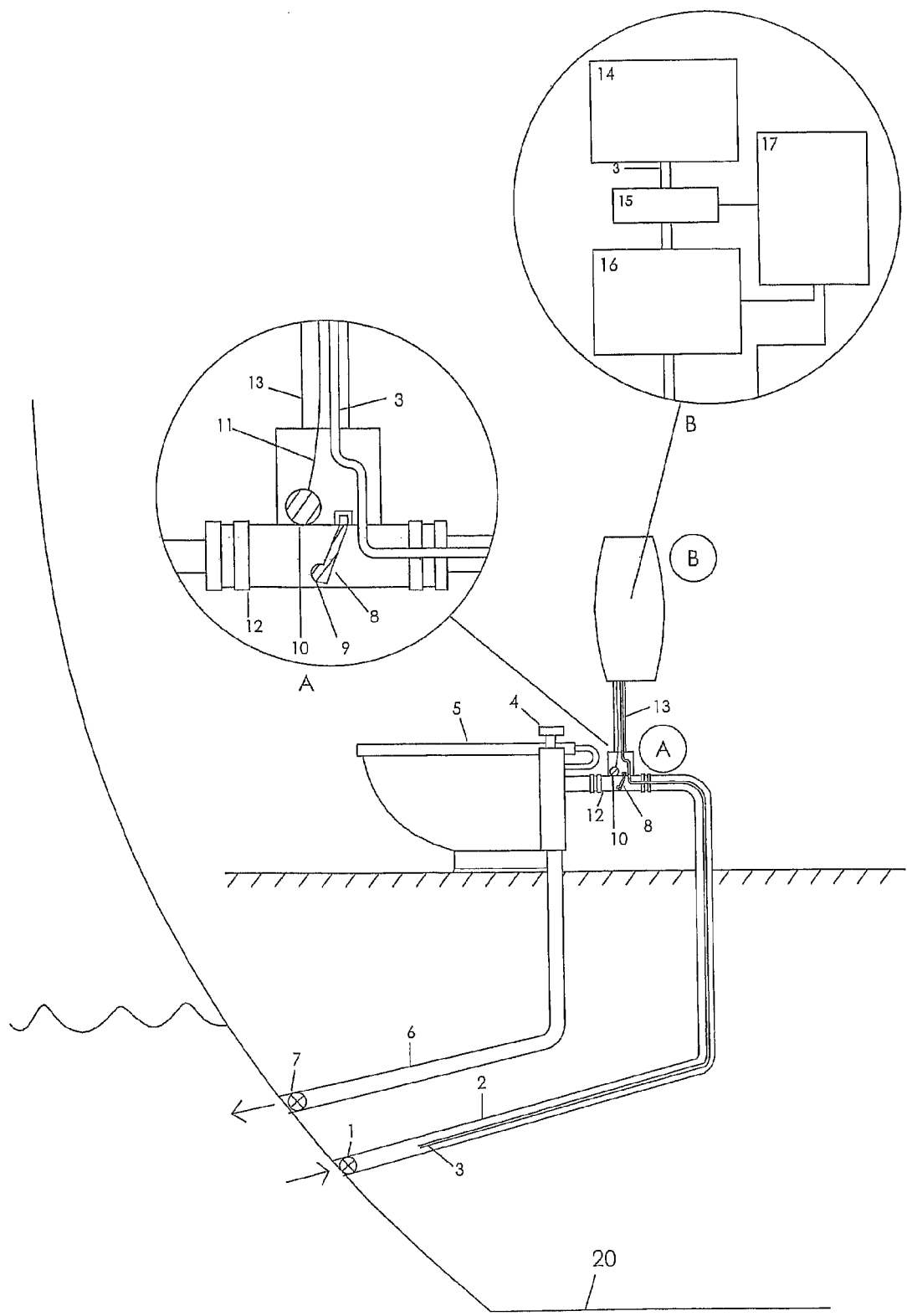
FIG. 1 depicts a cross sectional view through the hull of a craft, showing in particular the marine sanitising and deodorising device installed adjacent to a marine toilet bowl, which in use is flushed by sea or river or lake or canal water.

FIG. 1 shows a boat hull 20 with an inlet seacock 1 connected to a toilet flushing sanitation hose 2 conveying sea or river or lake or canal water to a marine toilet 5 via a flow detection manifold A. The flushing water is then pumped via the manual or electric toilet flushing pump 4, into the toilet bowl 5.

The foul or 'black' water from the marine toilet is then pumped via the dual action (or other) toilet flushing pump 4 from the marine toilet 5 to the sea via the sanitation hose 6 and the seacock 7, or to a holding tank* (not shown), depending on the vessel and its location.

The manifold A contains a flow detection device which in this embodiment has a rubber flap 8, containing a permanent magnet 9 and a reed switch 10 mounted outside the watertight area 12. When the toilet flushing pump 4 is actuated, water is drawn through the sanitation hose 2 and the manifold A, causing the rubber flap 8 to swing up so that the magnet 9 moves into close proximity to the reed switch 10, thereby operating the reed switch 10. The reed switch 10 is connected with electric wires 11 to the microprocessor 17 in the main body of the marine sanitising and deodorising device B, via a conduit 13.

In this embodiment the device contains a reservoir of disinfectant 14, a reservoir empty detection device 15, a micro dosing pump 16 and a microprocessor 17. Preferably the reservoir is made from plastic and has a resistance to chemicals, particularly disinfectants. The reservoir 14, detection device 15 and micro dosing pump 16 are connected together by microbore plastic tubing 3 which continues out of the device through the conduit 13 and in this embodiment, through the manifold A, into the inlet water sanitation hose 2. In this embodiment the microbore tube 3 continues to pass inside the sanitation hose 2, all the way through its passage to the seacock 1 but stops approximately 12 inches or 30 cms before the seacock 1.

In other embodiments the microbore tube 3 could pass externally from the main body of the marine sanitising and deodorising device B, or the conduit 13, and connect directly into the sanitation hose 2, 12 inches or 30 cms before the seacock 1.

The microprocessor 17 is connected to the reed switch 10, the reservoir empty detection device 15, the micro dosing pump 16 and a suitable power source (not shown) such as a 9 Volt PP3 battery or the boat's power supply.

When the toilet is flushed with the flushing pump 4, the reed switch 10 is operated by the swinging magnet 9 and the microprocessor 17 receives a signal to say that the flush cycle has commenced. This causes the microprocessor 17 to cycle through a series of algorithms, firstly a period of delay, then a sequence of running the micro dosing pump 16, causing disinfectant to be drawn from the disinfectant reservoir 14, through the detection device 15, the micro dosing pump 16 and into the microbore tubing 3, running to the inlet seacock 1.

Once primed with disinfectant, the small bore of the microbore tubing 3 remains full of disinfectant all of the time, because of meniscus action. This means that that when a small quantity of disinfectant is drawn into the system, an equal quantity is instantly pushed out of the open end of the microbore tubing 3, close to the seacock 1, regardless of the length of microbore tube 3.

Because the disinfectant is dosed into the toilet sanitation hose right at its start, close to the inlet sea cock 1, all of the flushing water throughout the whole length of the inlet sanitation hose 1, the toilet 5, its flushing pump system(s) 4 and the discharge hose 6, contains disinfectant and is maintained in a sanitized and odour controlled condition.

On certain occasions the craft may be subject to long continuous usage, such as a long voyage with a full crew on board. On these occasions the toilet(s) could be subject to heavy usage of 50 or more flushes per day, which would exhaust the disinfectant container quite quickly.

In these circumstances less disinfection to the system is required so the microprocessor 17 registers the high usage and reduces the amount of disinfectant dispensed each flush by reducing the timed period of operation of the micro dosing pump 16. This ecologically friendly feature reduces disinfectant usage and allows the disinfectant to last an acceptable period of time before refilling, during heavy usage.

Most craft are left unused for periods of time, during which the disinfectant in the inlet sanitation hose 2 can become diluted with the water outside the craft via the open sea cock 1. In this embodiment of the invention, when the toilet has not been used for a set period of days, the microprocessor 17 detects that the system has not been used and therefore runs the micro dosing pump 16 for a short period of time to re-introduce disinfectant into the inlet sanitation hose 2, where it disperses throughout the length of the inlet sanitation hose 2.

In this way the device maintains the sanitized and odour controlled condition in the inlet sanitation hose 2, even when the craft is left unused, so that when next flushed there is no foul smell introduced into the craft from the dead and decaying organisms and organic matter in the inlet sanitation hose, or from the rest of the toilet system.

The microprocessor 17 also monitors the empty refill detection device 15, so that when the marine sanitising and deodorising device requires the disinfectant refill to be replaced, it flashes a "Refill" LED on the front of the control unit B, when the toilet is being flushed.

In addition, the microprocessor also monitors the power supply battery (not shown), so that when the voltage is low and the battery needs to be replaced, the microprocessor flashes a "battery" indicating LED on the front of the control unit B, when the toilet is being flushed.

Figure 2:
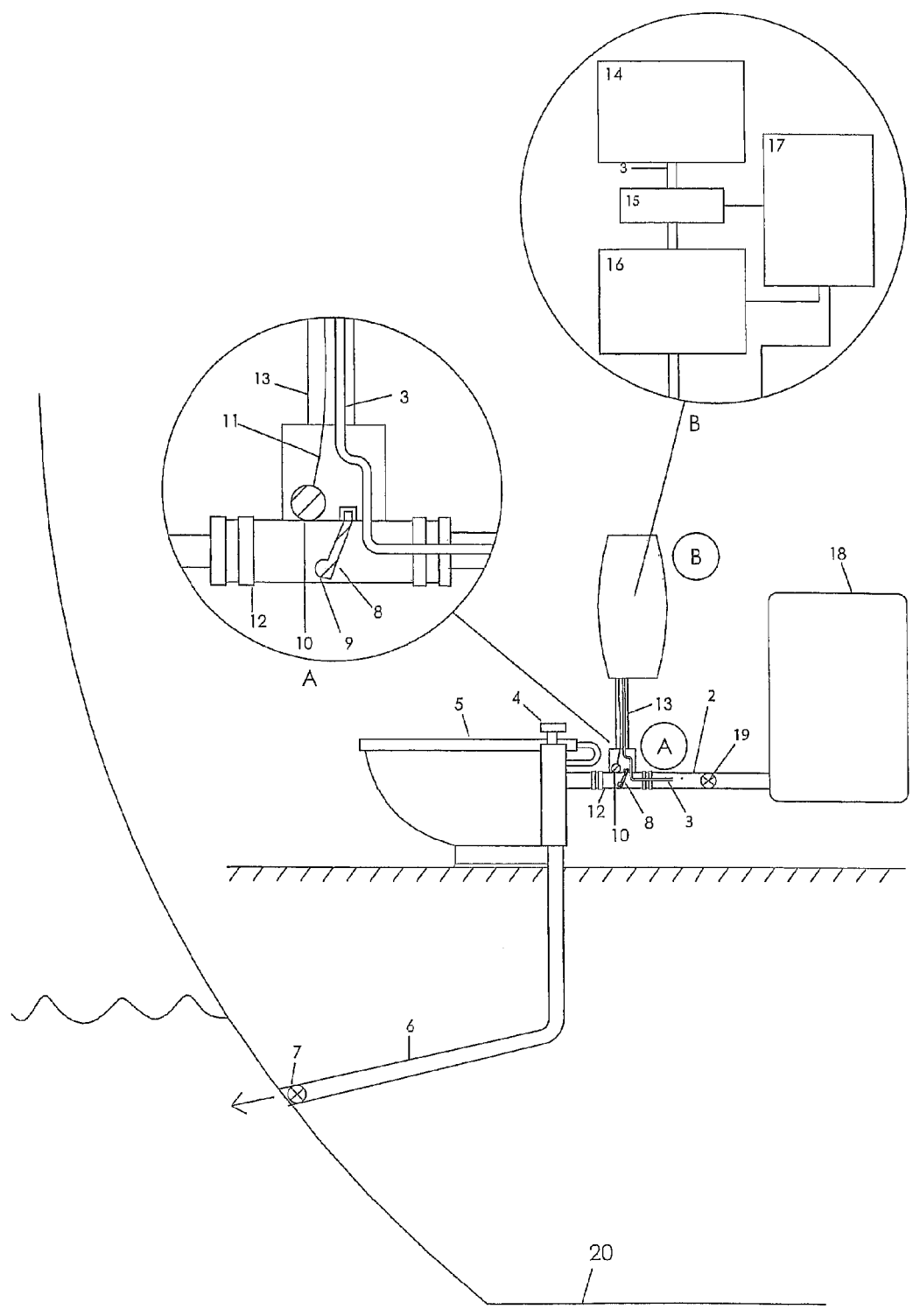
FIG. 2 depicts a cross sectional view through the hull of a craft, showing in particular the marine sanitising and deodorising device installed adjacent to a marine toilet bowl, which in use is flushed by water from the craft's onboard water tanks.

FIG. 2 shows a boat hull 20 with an on board water storage tank 18 connected to a toilet flushing sanitation hose 2, via a non return valve 19, conveying the water in the craft's water storage tank to a marine toilet 5 via the flow detection manifold A. The flushing water is then pumped via the manual or electric pump 4, into the toilet bowl 5.

The foul or 'black' water from the marine toilet is then pumped via the dual action, electric, or other pump 4 from the marine toilet 5 to the sea via the sanitation hose 6 and the sea cock 7, or to a holding tank* (not shown), depending on the vessel and its location.

The manifold A contains a flow detection device which in this embodiment comprises a rubber flap 8, containing a permanent magnet 9 and a reed switch 10 mounted outside the watertight area 12. When the pump 4 is actuated, water is drawn through the sanitation hose 2 and the manifold A, causing the rubber flap 8 to swing up so that the magnet 9 moves into close proximity to the reed switch 10, thereby operating the switch. The reed switch 10 is connected with electric wires 11 to the microprocessor 17 in the main body of the control unit B, via a conduit 13.

In this embodiment the device contains a reservoir of disinfectant 14, a reservoir empty detection device 15, a micro dosing pump 16 and a microprocessor 17. The reservoir 14, detection device 15 and pump 16 are connected together by microbore plastic tubing 3 which continues out of the control unit B through the conduit 13 and the manifold A, into the inlet water sanitation hose 2, where it terminates. The microprocessor 17 is connected to the Reed switch 10, the reservoir empty detection device 15, the micro dosing pump 16 and a suitable power source (not shown) such as a 9 volt PP3 battery or the boats power supply.

When the toilet is flushed, with the flushing pump 4, the reed switch 10 is operated by the swinging magnet 9 and the microprocessor 17 receives a signal to say that the flush cycle has commenced. This causes the microprocessor 17 to cycle through a series of algorithms, firstly a period of delay, then a sequence of running the micro dosing pump 16, causing disinfectant to be drawn from the disinfectant reservoir 14, through the detection device 15, the micro dosing pump 17 and into the microbore tubing 3, and on to the manifold A, where it terminates.

Once primed with disinfectant, the small bore of the microbore tubing 3 remains full of disinfectant all of the time, because of the surface tension of the liquid. This means that that when a small quantity of disinfectant is drawn into the system, an equal quantity is instantly pushed out of the open end of the microbore tubing 3, into the inlet sanitation hose 2.

Because the disinfectant is dosed into the toilet sanitation hose 2 before the manifold A, all of the flushing water in the inlet sanitation hose 2, the toilet 5, its flushing pump system(s) 4 and the discharge sanitation hose 6, contains disinfectant and is maintained in a sanitized and odour controlled condition.

On certain occasions the craft may be subject to long continuous usage, such as a long voyage with a full crew on board. On these occasions the toilet(s) could be subject to heavy usage of 50 or more flushes per day, which would exhaust the disinfectant container quite quickly.

In these circumstances less disinfection to the system is required so the microprocessor 17 registers the high usage and reduces the amount of disinfectant dispensed each flush by reducing the timed period of operation of the micro dosing pump 16. This ecologically friendly feature reduces disinfectant usage and allows the disinfectant to last an acceptable period of time before refilling, during heavy usage.

The microprocessor 17 also monitors the empty refill detection device 15, so that when the device requires the disinfectant refill to be replaced, it flashes a "Refill" LED on the front of the control unit B, when the toilet is being flushed.

In addition, the microprocessor also monitors the power supply battery (not shown), so that when the voltage is low and the battery needs to be replaced, the device flashes a "battery" indicating LED on the front of the control unit B, when the toilet is being flushed.

*Holding Tanks

It should be noted that where the discharge from a marine toilet is directed into a holding tank (not shown in these diagrams), the marine sanitising and deodorising device is not intended to disinfect the content of the holding tank. Holding tanks need to be properly vented so that their contents can naturally break down and the small eco-friendly quantities of biodegradable disinfectant dosed by the device will quickly biodegrade when held in contact with faecal matter and urine in a holding tank. The marine sanitising and deodorising device does not, therefore, effect or interfere with the normal operation or discharge of holding tanks.

The embodiments described above provide for the various elements of the marine sanitising and deodorising device to be substantially contained in a housing installed near the toilet and a manifold attached to the water inlet of the toilet. However, the different elements could be installed or contained individually or in different groupings in any suitable position or place to achieve the same result.

It is thus possible to provide a marine sanitising and deodorising device for a marine toilet system which overcomes malodorous and foul smelling problems associated with such toilets. The apparatus avoids the ecologically and environmentally unfriendly actions of boat owners flushing large quantities of powerful disinfectants (which are not easily biodegradable), through their toilets into the sea or other water courses. The device is quick, simple and easy to install and can sanitise all of the marine toilet system and associated pipe work without the disadvantage and danger of cutting, drilling or disconnecting hoses below the craft's waterline, as required by "dissolving block" type systems. This is advantageously achieved by use of the special microbore disinfectant tube, which preferably passes inside the toilet sanitation hose itself to or adjacent to the water inlet opening. The present invention also beneficially utilises intelligent microprocessor technology to continually dispense small exact doses of biodegradable disinfectant every time the toilet is flushed, and may also intelligently monitor toilet use to dispense small doses of disinfectant into the toilet system when the craft is not in use, thereby stopping malodorous and foul smells from decomposing organisms in the water of the toilet system and its associated sanitation hose. Alternatively or additionally, the apparatus may also provide intelligent monitoring of toilet use to adjust and reduce the amount of disinfectant dispensed when the craft's toilet is being heavily used, during long passages with a full crew. It is also possible to provide an apparatus which avoids the over or under disinfection caused by known "dissolving block" type sanitising systems. The device of the present invention is advantageous in that it is quick, simple and easy to refill, preferably with LED indication when refill is required. It also avoids the dangers and leakage problems when replacing "dissolving block" type systems below the craft's waterline. The invention also stops or greatly reduces the expensive replacement of marine toilet sanitation hose due to water born bacteria and other organisms migrating into and through the structure of the sanitation hose, causing malodorous and foul smells in the bilges of the craft. The craft's holding tanks, where used, are not affected and continue to work normally because of the precise and accurate micro dosing of the disinfectant or other sanitising fluid.

The embodiments described above are provided by way of examples only, and various other modifications will be apparent to persons skilled in the art without departing from the scope of the appended claims.

The invention claimed is:

1. A marine sanitising and deodorising device for a marine toilet system having a water inlet conduit extending therefrom to a water inlet valve in a hull of a boat, said device comprising:
   a sanitising fluid reservoir which contains sanitising fluid, wherein the sanitising fluid reservoir is at or adjacent to a discharge end of the water inlet conduit;
   a sanitising fluid dose variable and controllable pump which discharges a predetermined dose of sanitising fluid from the reservoir into the water inlet conduit of the marine toilet system, wherein the dose variable and controllable pump has a microbore conduit which enters into the water inlet conduit at or adjacent to the discharge end of the water inlet conduit;
   a flow detector which detects the flow of water within the water inlet conduit; and a controller which controls the dose variable and controllable pump upon flow detection by the in use flow detector;

wherein the microbore conduit has an outlet that is at or proximate to the water inlet valve associated with the water inlet conduit, so that the sanitising fluid is delivered from the sanitising fluid reservoir to or proximate to the water inlet valve against a flow direction of water in the water inlet conduit.

2. The marine sanitising and deodorising device as claimed in claim 1, in which the dose variable and controllable pump is a micro-dosing pump.

3. The marine sanitising and deodorising device as claimed in claim 1, in which the controller includes a microprocessor which varies the dosage of the micro-dosing pump.

4. The marine sanitising and deodorising device as claimed in claim 1, in which the flow detector is arranged to be at least partially disposed within the water inlet conduit.

5. The marine sanitising and deodorising device as claimed in claim 4, in which the flow detector includes a moveable gate and a reed switch.

6. The marine sanitising and deodorising device as claimed in claim 5, in which the moveable gate includes a hinge, said in use moveable gate pivoting about said hinge when liquid flows through the water inlet conduit.

7. The marine sanitising and deodorising device as claimed in claim 6, in which the moveable gate has a magnet at a free end which activates a magnetic portion of the reed switch.

8. The marine sanitising and deodorising device as claimed in claim 1, in which the controller includes a status device which detects and indicates an amount of sanitising fluid within the reservoir.

9. The marine sanitising and deodorising device as claimed in claim 8, in which the status device is adapted to emit an alert when the reservoir is or is substantially empty.

10. A marine sanitising and deodorising toilet system comprising:
a toilet bowl;
at least one pump which controls the flow of water into and/or out of the toilet bowl;
a water inlet conduit having a discharge end which delivers water to the toilet bowl;
a waste outlet conduit which moves waste from the toilet bowl;
a marine sanitising and deodorising device;
a sanitising fluid dose variable and controllable pump of the device being in fluid communication with the water inlet conduit which discharges sanitising fluid therein when activated by a controller upon flow detection, wherein the sanitising fluid dose variable and controllable pump has a microbore conduit which enters into the water inlet conduit at or adjacent to the discharge end, and wherein the microbore conduit extends along all or substantially all of a longitudinal extent of the water inlet conduit; and
a sanitising fluid reservoir at or adjacent to the discharge end of the water inlet conduit;
wherein the microbore conduit has an outlet that is at or proximate to a water inlet valve associated with the water inlet conduit, so that the sanitising fluid is delivered from the sanitising fluid reservoir to or proximate to the water inlet valve against a flow direction of water in the water inlet conduit.

11. The marine sanitising and deodorising toilet system as claimed in claim 10, further comprising a ventable holding tank which is in liquid communication with the water inlet conduit enabling transport of the water thereto.

12. The marine sanitising and deodorising toilet system as claimed in claim 10, forming part of a marine craft having a hull, an outlet of the waste outlet conduit being provided in the hull and below a waterline of the hull.

* * * * *